United States Patent [19]

Hillman et al.

[11] Patent Number: 4,756,884

[45] Date of Patent: Jul. 12, 1988

[54] CAPILLARY FLOW DEVICE

[75] Inventors: Robert S. Hillman, Cupertino; Michael E. Cobb, Sunnyvale; Jim Allen, Los Altos; Ian Gibbons, Menlo Park; Vladimir Ostoich, San Jose; Laura J. Winfrey, Belmont, all of Calif.

[73] Assignee: Biotrack, Inc., Mt. View, Calif.

[21] Appl. No.: 880,793

[22] Filed: Jul. 1, 1986

Related U.S. Application Data

[63] Continuation-in-part of Ser. No. 762,748, Aug. 5, 1985, abandoned.

[51] Int. Cl.⁴ ............................................. G01N 11/04
[52] U.S. Cl. ........................................ 422/73; 422/81; 422/82; 435/810
[58] Field of Search ................... 422/68, 72, 73, 81, 422/312, 82, 57, 102; 73/55, 56, 61.1 R; 356/28, 28.5; 436/69, 180; 435/810

[56] References Cited

U.S. PATENT DOCUMENTS

| | | |
|---|---|---|
| 3,690,836 | 9/1972 | Buissiere et al. . |
| 3,744,975 | 7/1973 | Mailen ................................. 422/72 |
| 3,799,742 | 3/1974 | Coleman . |
| 3,856,470 | 12/1974 | Cullis et al. ............................ 422/72 |
| 3,873,217 | 3/1975 | Anderson et al. ..................... 422/72 |
| 3,898,982 | 8/1975 | Katsuda . |
| 3,899,296 | 8/1975 | Mailen et al. ......................... 422/72 |
| 3,901,658 | 8/1975 | Burtis et al. .......................... 422/72 |
| 3,915,644 | 10/1975 | Walvren ................................ 422/68 |
| 4,088,448 | 5/1978 | Lilja et al. . |
| 4,244,916 | 1/1981 | Guigan ................................. 422/72 |
| 4,279,862 | 7/1981 | Bretaudiere et al. ................. 422/72 |
| 4,284,602 | 8/1981 | Kelton et al. ......................... 422/72 |
| 4,690,899 | 9/1987 | Klose et al. ........................ 422/102 |

OTHER PUBLICATIONS

Bowman et al., Science (1967) 158:78–83.

Primary Examiner—Barry S. Richman
Assistant Examiner—Jill Johnston
Attorney, Agent, or Firm—Leydig, Voit & Mayer

[57] ABSTRACT

Methods and devices are provided involving at least one chamber, at least one capillary, and at least one reagent involved in a system providing for a detectable signal. As appropriate, the devices provide for measuring a sample, mixing the sample with reagents, defining a flow path, and reading the result. Of particular interest is the use of combinations of specific binding pair members which result in agglutination information, where the resulting agglutination particles may provide for changes in flow rate, light patterns of a flowing medium, or light absorption or scattering. A fabrication technique particularly suited for forming internal chambers in plastic devices is also described along with various control devices for use with the device.

12 Claims, 3 Drawing Sheets

CAPILLARY FLOW DEVICE

CROSS-REFERENCE TO RELATED APPLICATIONS

This application is a Continuation-in-part of application Ser. No. 762,748, filed Aug. 5, 1985, now abandoned and refiled as File Wrapper Continuation Ser. No. 016,506 on Feb. 17, 1987;

BACKGROUND OF THE INVENTION

1. Field of the Invention

This invention is related to testing devices having internal chambers into which fluids are drawn by capillary action, to methods of using such devices, and to methods of manufacturing such devices.

2. Background of the Invention

In the development of the diagnostics field, there has been explosive growth in the number of substances to be determined. For the most part, the medical field has looked to clinical laboratories for these determinations. The clinical laboratories have been dependent upon expensive sophisticated equipment and highly trained technical help to fulfill the manifold needs of the medical community. However, in a highly automated clinical laboratory, there is substantial need to perform one or a few assays on a station basis with minimum equipment.

There is also an expanding need for having analytical capabilities in doctors' offices and in the home. There is a continuing need to monitor the level of drug administered to people with chronic illnesses, such as diabetics, asthmatics, epileptics, and cardiac patients, as it appears in a physiological fluid, such as blood. Tests of interest include prothrombin time, potassium ion, and cholesterol. Determining red-bloodcell count is also a common test. In the case of diabetic patients, it is necessary to determine sugar level in urine or blood.

Numerous approaches have been developed toward this end, depending to varying degrees on instrumental or visual observation of the result. Typical of these are the so called "dip-stick" methods. These methods generally employ a plastic strip with a reagent-containing matrix layered thereon. Sample is applied to the strip and the presence or absence of a analyte is indicated by a color-forming reaction. While such devices have proven useful for the qualitative determination of the presence of analytes in urine and can even be used for rough quantitative analysis, they are not particularly useful with whole blood because of the interferring effects of red blood cells, nor are they useful for making fine quantitative distinctions. Accordingly, there remains a need for the development of methods and devices capable of analyzing whole blood and other complex samples rapidly with a minimum of user manipulations.

Many small devices in the analytical area depend on the use of plastics having specified characteristics, such as optical transparency and machinability. Machinability refers here to the ability to produce chambers, channels, and openings of prescribed dimensions within the plastic device. Although numerous plastic devices have been devised, the fabrication techniques are not interchangeable because of differences in the devices or the desired measuring result. This is particularly true for devices containing channels or other chambers of stall dimensions internally in the plastic material. The fine channels are difficult to produce entirely within a plastic matrix and, if prepared in the surface of two matrices to be sealed to each other, are readily deformed during many sealing processes.

Accordingly, there remains a need for new devices for use in methods of rapid analytical testing and for new methods of producing these devices.

BRIEF DESCRIPTION OF THE RELEVANT LITERATURE

Powers et al., *IEEE Trans. on Biomedical Engr.* (1983) BME-30-228, describes detecting a speckle pattern for determining platelet aggregation, as does Reynolds, *Light Scattering Detection of Thromboemboli*, Trans. 11th Annual Mtg. of the Soc. for Biomaterials, San Diego, CA, Apr. 25–28, 1985. Reynolds and Simon, *Transfusion* (1980) 20:669–677, describes size distribution measurements of microaggregates in stored blood. Of interest in the same area are U.S. Pat. Nos. 2,616,796; 3,810,010; 3,915,652; 4,040,742; 4,091,802; and 4,142,796. U.S. Pat. No. 4,519,239 describes an apparatus for determining flow shear stress of suspensions in blood. Ab Leo sells the HemoCue TM device for measuring hemoglobin. Also, see U.S. Pat. No. 4,088,448, which describes a cuvette for sampling with a cavity which is defined in such a manner as to draw into the cavity a sample in an amount which is exactly determined in relation to the volume of the cavity by capillary force. Numerous plastic assembly techniques, particularly ultrasonics plastic assembly, is described in a book of the same name published by Branson Sonic Power Company, Danbury, Connecticut, 1979. Gallagan, *Plastics Engineering*, August 1985, 35–37 also describes ultrasonic welding of plastics. U.S. Pat. No. 3,376,208 describes corona discharge, although for a different purpose. U.S. Pat. No. 3,376,208 describes the use of an electric discharge to modify a film surface. A device used to transport liquids by capillary flow is described in U.S. Pat. No. 4,233,029.

SUMMARY OF THE INVENTION

The present invention provides fabrication techniques, the resulting devices, and techniques related to the use of such devices in which a defined chamber or channel is prepared within the internal space of a solid device. The devices typically call for the use of capillary force to draw a sample into the internal chambers of a plastic device. Such capillary flow devices, particularly capillary flow devices designed for a constant flow rate, typically include at least one capillary acting as a pump, usually for controlling the volume of the sample and the time period for reaction, a chamber, an inlet port, a vent, and a reagent in proximity to at least one surface of the device. The capillary and chamber provide for capillary flow due to surface action and for mixing of the assay medium with the reagent. The reagent is part of a detection system, whereby a detectable result occurs in relation to the presence of an analyte. The device and the corresponding method can be used with a wide variety of fluids, particularly physiological fluids, for detection of drugs, pathogens, materials endogenous to a host, or the like. In most cases an optical measurement is being made, which requires the selection of a transparent material. Devices of unusually advantageous properties can be prepared by injection molding acrylonitrilebutadiene-styrene copolymer (ABS) so as to form a depression of defined dimensions in the surface of at least one face of the polymer, increasing wettability of the surface in at least those portions defined by the depression using either plasma etching or corona discharge, providing energy directing ridges projecting from the surface of the plastic adjacent to the depression or in a second piece of plastic so shaped as to contact the area adjacent to the depressions in the plastic surface, and ultrasonically welding the two plastic surfaces so as to produce an internal chamber or channel of defined dimensions having an air-tight seal around the perimeter of the resulting chamber. Although the fabrication method can be used to produce internal chambers of any dimension, the method is particularly suitable for the production of chambers and channels of small dimensions that are suitable for inducing capillary flow.

DESCRIPTION OF THE SPECIFIC EMBODIMENTS

Figure 1A:
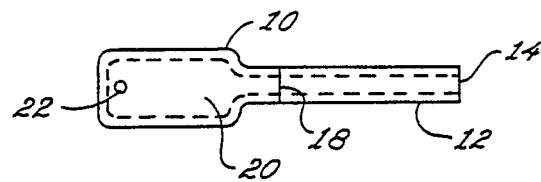
FIGS. 1A and 1B are plan views of two embodiments of the subject invention, FIG. 1A employing a single capillary and chamber and FIG. 1B employing two capillaries separated by a chamber.

This invention provides devices and methods, where the devices rely upon capillaries, chambers, and orifices to pump fluids; to control measurement of fluids, reaction times, and mixing of reagents; and to determine a detectable signal. By varying the path through which the fluid flows, one can provide for a variety of activities, such as mixing, incubating and detecting. The methods may involve the binding of homologous members of a specific binding pair, resulting in complex formation. The complex formation can provide for a variety of events which can be detected by instrumentation or visual means. Alternatively, the methods may involve chemical reactions, for example, the detection of glucose or serum enzymes, which result in a detectable change in the sample medium. Since the devices rely upon capillaries and other chambers to control movement of fluids, accurate control of the dimensions of the internal chambers is essential. The fabrication techniques described later provide this accurate control.

The sample may be a fluid which is used directly as obtained from the source or may be pretreated in a variety of ways so as to modify its character. The sample will then be introduced into the device through an inlet port, which may introduce the sample into a chamber or a capillary. The sample will then transit the device passing through the capillary(ies) or chamber(s), where the sample will encounter one or more reagents, which reagents are involved in a system which produces a detectable signal. By having orifices which connect the pathway to the atmosphere at one or more sites, one can terminate the flow up to that site, so that the medium may be incubated for various times or movement stopped subject to the initiating movement, for example, immediately prior to measurement.

Any liquid sample may be employed, where the sample will have a reasonable rate of flow due to the pumping of the capillary action. It is to be understood the capillary action is the sole driving force, relying on the surface action between the surface and the fluid. Where the sample is too viscous, it should be diluted to provide for a capillary pumping rate which allows for the desired manipulations, such as mixing, and for a reasonable flow time which will control the time period for the assay.

The sample may be derived from any source, such as a physiological fluid, e.g., blood, saliva, ocular lens fluid, cerebral spinal fluid, pus, sweat, exudate, urine, milk, or the like. The fluid may be subjected to prior treatment, such as preparing serum from blood, diluting pus, saliva, or the like; the methods of treatment may involve concentration, by filtration, distillation, dialysis, or the like; dilution, filtration, inactivation of natural components, concentration, chromatography, addition of reagents, chemical treatment, etc.

Besides physiological fluids, other liquid samples may be employed where the component(s) of interest may be either liquids or solids and the solid(s) dissolved in a liquid medium. Samples of interest include process streams, water, soil, plants or other vegetation, air, and the like.

The analytes of interest are widely varied depending upon the purpose of the assay and the source. Analytes may include small organic molecules, such as drugs, hormones, steroids, neurotransmitters, growth factors, commercial chemicals, degradation products, drugs of abuse, metabolites, catabolites, etc. Large organic molecules may be determined, such as nucleic acids, proteins, polysaccharides, or the like. Aggregations of molecules may also be of interest, particularly naturally-occurring aggregations such as viroids, viruses, cells, both prokaryotic and eukaryotic, including unicellular microorganisms, mammalian cells such as lymphocytes, epithelial cells, neoplastic cells, and the like.

Phenomena of interest which may be measured may be indicative of physiological or non-physiological processes, such as blood clotting, platelet aggregation, complement-mediated lysis, polymerization, agglutination, etc.

The sample medium may be the naturally-occurring medium or the sample introduced into a liquid meidum which provides for the desired characteristics necessary for the capillary pumping action and the detectable signal. For the most part, aqueous media will be employed and to that extent aqueous media will be exemplary of the media employed in the subject invention. The aqueous media may be modified by the addition of a variety of miscible liquids, particularly oxygenated organic solvents, such as lower alkanols, dimethyl formamide, dimethyl sulfoxide, acetone, or the like. Usually, the solvents will be present in less than about 40 volume percent, more usually in less than about 20 volume percent. Besides other solvents, other liquid or solid additives may be included in the medium to modify the flow or other properties of the medium, such as sugars, polyols, polymers, detergents, surfactants and the like, involved with changes in wetting, adherence, laminar flow, viscosity, and the like.

In addition to the components mentioned above, other additives may be included for specific purposes. Buffers may be desirable to maintain a particular pH. Enzyme inhibitors may be included. Other reagents of interest are antibodies, preservatives, stabilizers, activators, enzyme substrates and cofactors, oxidants, reductants, etc. In addition, filtration or trapping devices may be included in the device pathway, so as to remove particles above a certain size. The particles may include cells, viruses, latex particles, high molecular weight polymers, nucleic acids, by themselves or in combination with proteins, e.g., nucleosomes, magnetic particles, ligand or receptor containing particles, or the like.

The sample may provide the detectable component of the detection system or such component may be added. The component(s) will vary widely depending upon the nature of the detection system. One detection method will involve the use of particles, where particles provide for light scatter or a change in the rate of flow. The particles may be cells, polymeric particles which are immiscible with the liquid system, latex particles, charcoal particles, metal particles, polysaccharides or protein particles, ceramic particles, nucleic acid particles, agglutinated particles, or the like. The choice of particle will depend upon the ease of detection, the dispersability or stability of the dispersion, inertness, participation in the change in flow, and the like. Particle sizes will generally be from about $0.1$–$100\mu$, more usually from about $5$–$15\mu$. Other phenomena which may be detected include changes in color, light absorption or transmission, fluorescence, change in physical phase, or the like.

The neat sample or formulated sample will be introduced into the entry port into the receiving unit of the device. The receiving unit may be a capillary or a chamber. The receiving unit may be used to measure the particular sample volume or may simply serve to receive the sample and direct the sample to the next unit of the device. The capillary units serve a variety of functions, including a measuring device for volume measurement, a metering pump for transferring liquid from one chamber to another, flow controller for controlling the rate of flow between chambers, mixer for mixing reagents, and detecting unit for detection. For the most part, the capillaries will serve as transfer units, flow control units and detection units. The chambers and capillaries may be used to define different events, e.g., areas of reaction, or different structural entities in certain embodiments of the method.

The capillaries will usually be of a substantially smaller cross-section or diameter in the direction transverse to the direction of flow than the chambers. The cross-section or length in the direction of flow may be similar or may differ by a factor of ten or more depending on the function of the capillary and the chamber. Capillaries will usually have diameters in the range of about 0.01 mm to 2 mm, usually about 0.1 mm to 1 mm. The length of the capillary, particularly the first capillary in the pathway, more particularly the first capillary when it is joined to the entry port, will be at least about 3 mm, more usually at least about 5 mm, and may be 1 cm or more, usually not more than about 2 cm, while subsequent capillaries may be shorter or longer, frequently at least one being longer, being as long as 10 cm, usually not exceeding about 5 cm.

The first capillary will initially control the rate of flow into the chamber which will usually serve as the reaction chamber. Thus, the capillary may aid in the control of the time with which the assay medium is in contact with reagent contained within or bound to the walls of the capillary and/or reaction chamber and the progress of the assay medium through the chamber. Other components which may affect the rate of flow in the chamber include baffles, walls or other impedimenta in the chamber, the geometry of the chamber, the reagent in the chamber and the nature of the surfaces in the capillary and chamber. Since in many instances the initial contacting of the assay medium and the reagent could affect the results, it is desirable that the contact be sufficiently slow that equilibrium can occur, as to dissolution, reaction, etc.

The capillary control and use of relatively thin heat conductive walls allows for rapid heat transfer and isothermal conditions, or alternatively, thick walls can provide for adiabatic conditions. Thus, the small volume of fluid in the chambers and capillaries permits for rapid heat exchange or efficient thermal insulation. In addition, the thin capillaries permit optical measurements, particularly based on transmission of light, with optically dense samples, e.g., whole blood. There is the further opportunity for rapid efficient mixing, where by sonication the whole sample can be uniformly mixed.

The capillary provides the sole driving source for the movement of liquid through the device. Accordingly, careful fabrication of the capillary to exact dimensions is required. The device is normally employed in the horizontal position, so that gravity does not affect the flow rate. The composition of the walls of the capillary are selected so as to provide the desired degree of wetting and surface tension or the walls are modified to provide the desired physical properties. The device is employed without ancillary motive force, such as pumps, gravity or the like.

The chambers also have a variety of functions, serving as protection for the reagent(s) mixing chambers for dissolution of reagent and/or reaction with reagent, volume measurement, incubation and detection, where the detectable signal is other than a signal associated with flow, and the like. The chambers will be primarily employed for mixing, incubating and for holding of liquids.

Depending upon the particular system, the length of the capillaries, their cross-sectional area, the volumes of the various chambers, and their length and shape, may be varied widely. One constraint on each of the capillaries is the necessity for their function providing capillary pumping action for flow. Therefore air leaks in the space surrounding the capillary (except for designed access ports) cannot be tolerated. In many instances, the chambers will also provide for capillary action while the flow rate which will be affected by the nature of the capillary surface will be primarily determined by the capillary action of the capillaries.

In order to minimize the handling of reagents by the user of the device, the reagents may be supplied within the device, whereby mixing with the reagents occurs in the device. The reagents may be present either diffusively or non-diffusively bound to the surface of the device, that is, adhered, absorbed, adsorbed or covalently-linked, so that the reagent may become dissolved in the fluid or may remain fixed to the surface. Where the reagents are diffusively bound (non-covalently and weakly bound), a variety of situations can be accommodated. One situation is where the liquid front dissolves all of the reagent, so that the liquid front receives a high concentration of the reagent and most of the reaction occurs at the liquid front. A second situation would be with an excess of a reagent of limited solubility. In this situation, the reagent may be present in the liquid medium at a substantially uniform concentration. A third situation is to have a deficiency of a reagent of limited solubility, so that only the early portion of the fluid will have a relatively constant reagent concentration. In many instances it is essential that the reagent be present in a defined area or reaction chamber, which makes fabrication of an internal chamber followed by later addition of reagent virtually impossible.

While for the most part, the reagent will be present in one or more units of the device, reagents also can be mechanically introduced by various techniques. For example, by employing a septum, a syringe may be employed for introducing a reagent. Alternatively, one could have an orifice and use an eyedropper or other means for introducing liquid reagent into the unit. Usually, unless essential, these alternative techniques will be avoided.

The reagent will vary depending upon the nature of the sample, the analyte, and the manner in which the detectable signal is generated. A chemical reaction will occur due either to the formation of covalent bonds, e.g., oxidation or reduction, hydrolysis, etc., or non-covalent bonds, e.g., complex formation between ligand and receptor, including complex formation between nucleic acids.

The same or different reagent may be present in the various units, so that successive reactions can occur or a reagent continually supplied into the moving medium. Also, one could have a plurality of chambers and capillary channels. Frequently, the first unit will have a reactant. The chambers can be varied in size and purpose, providing the varying incubation times, varying reaction times, mixing of media from different capillaries, or the like. Any number of chambers may be employed, usually not exceeding six. more usually not exceeding about four, where the chambers may be in series or parallel. The size of the unit, either capillary or chamber, can be particularly important, where the reagent is fixed, so that the residence time in contact with the reagent will be affected by the area of the reagent contacted by the assay medium.

By employing various filtration or trapping devices (e.g., mechanical or magnetic), one can inhibit the transfer of particles from a capillary channel to a chamber or vice versa. In this way, red cells can be removed from blood, various components of the sample may be removed, or by employing divergent channels, one channel can have particles removed and the particles retained in the other channel where the two results may be of interest.

Arbitrarily, the use of the device will be divided into two different concepts. The first concept will involve a characteristic other than a change in flow rate. For the most part, this will involve the absorption, scatter or emission of light. A wide variety of protocols and reagents are available which provide for a change in the measured light, as a result of absorption, scatter or emission, in relation to the amount of analyte in the sample.

Labels which may be employed include enzymes, in combination with substrates, cofactors or inhibitors, fluorescers, combinations of fluorescers and quenchers, dyes, or the like. In some instances a chemical reaction occurs as a result of the presence of the analyte or with the analyte, which provides a detectable signal. By employing appropriate protocols, the amount of absorption or emission of light in the detection unit can be directly related to the amount of analyte in the sample.

Detection of a change in the rate of flow may be the signal which results from the reaction of the label or may be the result of a combination of a plurality of entities, which affect the rate of flow. The change in flow rate may be as a result of agglutination, polymerization, complex formation between high molecular weight compounds or aggregations, or the like.

The measurement of light, e.g., scatter, can be used to measure a change in the size population. This can be particularly useful for measurement of agglutination, clumping, clot formation or dissolution, and the like. A laser is able to distinguish particle size without a change in the flow rate. Small particles have a low frequency and a high amplitude; large particles (agglutinated particles) have a lower frequency (fewer total particles) and a higher amplitude (each particle is larger). Thus the change in particle size distribution may be detected by integrated noise employing known circuitry.

Various situations can be involved where the assay medium may have no particles (entities capable of scattering) or have particles, such as cells, latex beads and the like, where the result of the reaction is to change the particle size distribution, including going from no particles to the formation of particles. There is also the opportunity to begin with particles, e.g., blood clots, and as a result of the reaction reduce the size and number of particles, e.g., dissolve the blood clots.

Because of the enormous diversity of protocols which are presently available which can be employed in the subject methods and devices, only a few will be illustrative and reference will be made to numerous patents which describe different protocols.

Protocols which may find use include those found in U.S. Pat. Nos. 3,817,837; 3,839,153; 3,998,943; 3,935,074; 4,174,834; 4,233,402; 4,208,479; 4,235,869; 4,275,149; 4,287,300, etc., the disclosure of these patents relating to protocols being incorporated herein by reference.

In a first exemplary protocol, a fluorescence measurement may be made, where one has a single capillary as the inlet, with the capillary coated with antibody to analyte. The sample is diluted with a buffered reagent containing a conjugate of analyte with fluorescer, whereby all of the fluorescent reagent will become bound in the capillary in the absence of any analyte in the sample. The capillary is then introduced into the sample and an amount of liquid withdrawn up to an indexed point on the capillary, whereby the capillary is then withdrawn from the sample and the liquid allowed to progress into the chamber. When the chamber is partially or completely full, the fluorescence of the chamber may then be read as indicative of the amount of analyte in the sample.

With enzymes, one could either vary the protocol or the device to prevent premature interaction between the enzyme and its substrate or inhibitor. Where a simple two-unit device is employed, employing a capillary and chamber, one could provide for using a combination of enzymes, referred to as channeling, where the product of one enzyme is the substrate of the other enzyme. In this manner, one could have in one unit a second enzyme combined with the substrate of the first enzyme, while the second unit having the first enzyme combined with the substrate of the second enzyme.

One could modulate the reaction by various means. For example, one could have antibody to analyte in the first unit and combine the sample with a buffered solution of antibody-first enzyme inhibitor conjugate. Thus, the amount of enzyme inhibitor which would enter the second unit would be related to the amount of analyte in the sample. Instead of having a two-unit system, one could have a three-unit system, where the first unit mixes the sample with the enzyme inhibitor conjugate avoiding the necessity to combine the sample with a liquid medium. Where the sample is colored, such as blood, it may be necessary to filter out or trap red blood cells, to allow for development of color or fluorescence or to find a wavelength range, where one can read the development of a particular light-absorbing material.

By employing a plurality of units, one can use a single enzyme, where the enzyme is conjugated to the analyte. By having enzyme-analyte conjugate in a first unit, followed by antibody to anlayte in a second unit and employing a third unit containing enzyme substrate as the reaction chamber, the measurement can be made in the third unit.

By employing combinations of filters and particles one could also achieve similar effects. For example, one can employ enzyme analyte conjugates in the first unit which completely dissolve in the assay medium. A second unit may then contain the particles containing antibody to the analyte. The amount of enzyme-analyte conjugate which binds to the antibodies will be dependent upon the amount of analyte in the sample. By having a filter at the exit of the second unit, all of the particles will be trapped at the filter, and only enzyme conjugate which is unbound will pass through the filter to the third unit. The third unit may then contain the enzyme substrate, so that reaction of the enzyme with the substrate can be monitored.

For the detection of change in flow rate, a wide variety of systems may be employed. Of particular interest is the natural system involving clotting, which is convenient when the sample is a blood sample. Thus, by adding one or more components of the clotting cascade or a component which activates the naturally-occuring components present, the clotting can provide for a change in the flow rate. Particularly, these reagents may include thromboplastin, factors I, II, IV, V, VII, VIII, IX, X, XI and XII. These components can be added individually or in combination. Particular combinations include factors of the intrinsic pathway (VIII, IX, XI and XII) or extrinsic pathway (III, VII) with the common pathway factors I, II, V, X, XIII. The clotting assay can be used to determine a wide variety of analytes of interest. The clotting assay may be used for the detection of the presence of anti-clotting agents or clotting agents. In addition, the clotting assay can be used for the detection of the level of a particular component required for clotting or a componenet involved in the dissolving of clots. Illustrative analytes include the various factors indicated above, warfarin, tissue plasminogen activator, heparin, streptokinase, Vitamin K, antiplatelet drugs, protamine sulfate, etc.

The clotting assay can also be used to measure any analyte of interest by having the analyte associated with a factor necessary for clotting. For example, by conjugating thromboplastin to a compound capable of competing with the analyte for a receptor, where the thromboplastin-receptor complex is inactive, one could determine the presence of the analyte. The sample would be mixed with the receptor for the analyte so that the binding sites of the receptor would be occupied by any analyte present. The thromboplastin conjugated to the analyte or mimetic analog would be the reagent in the reaction chamber. All the other components necessary for clotting would be included in the sample along with the antibodies for the analyte, where such other components were not naturally present in sufficient amount in the sample. The receptor sites which were not occupied by analyte would bind to the analyte conjugated to the thromboplastin where the resulting specific binding complex would lack thromboplastin activity. The remaining uncomplexed thromboplastin conjugate would be active and initiate clotting. By employing appropriate standards, one could relate the time to flow stoppage to the amount of analyte in the sample. Or, one could provide that flow stoppage did or did not occur with an amount of analyte above a threshold level.

Besides coagulation, agglutination, precipitation, or plug formation by other means, or, as appropriate, increasing viscosity can be used as part of the detection scheme.

For plug formation or slowing of flow by other than clotting, particles will usually be included in the medium which become cross-linked in relation to the amount of analyte present. This can be achived by employing receptors and ligands specific for the receptor so that non-covalent binding provides for multiple linkages between particles with a resulting cross-link structure which can serve as a plug. By using such particles as *S. aureus,* which specifically binds to immune complexes, red blood cells, synthetic or naturally-occurring particles to which ligands, rheumatoid factor, antibodies, naturally-occurring receptors, or the like, are conjugated, the crosslinking of the particles can be retarded or enhanced by the presence or absence of the analyte. Thus, in the case of antigens, the antigen may serve as a bridge between different antibodies, while in the case of haptens, individual haptens may inhibit the crosslinking resulting from a polyhaptenic molecule.

Various illustrations can be made of the different combinations which may be employed in the flow modulation methods of the subject invention. For example, the reagents could include an agarose bead to which is bound polyclonal antibodies to an antigen of interest or monoclonal antibodies where different particles are specific for different epitopic sites of the antigen. The sample need only include the detection component and any of the analyte which may be present. The sample would mix with the antibody-conjugated particles in the reaction unit and then flow into the exit unit. The presence of the analyte would result in cross-linking of the particles with large amorphous particles providing a greater drag on flow smaller particles. As the accretion of particles increased, ultimately a plug would form and flow would stop. In the case of haptens, the sample could be combined with antibodies to the haptens. The reagent could be hapten conjugated to porous glass beads. Available antibody would be capable of cross-linking the hapten-conjugated beads so as to ultimately provide a plug which would inhibit further flow.

Similar techniques could be used with hemagglutination where the particle is a red blood cell to which particular antigens are or have been bound. A sample which might contain cells having as part of their surface membrane the same antigen would be combined with the antigen conjugated red blood cell particles. The reagent would be antibody to the antigen. The rate of formation of the plug would vary depending upon whether cells containing the same antigen were present or absent.

A further illustration would involve polymers to which are attached polyclonal antibodies, where the polymers are selected so as to have only moderate solubility in the assay medium. Binding to antigenic bridges would result in desolubilization.

The polymers could be conjugated with nucleic acid sequences complementary to preselected sequences. The sequences would not be complementary to the nucleotide sequence of interest or to each other. The sample could be a lysate of a virus or pathogenic organism in an appropriate aqueous medium, where the genomic polynucleotides could be sheared. The sample would be combined with the polymeric reagents. The sample would then react in the reaction chamber with a nucleotide sequence which was a hybrid having a sequence complementary to the nucleic acid sequence of interest and a sequence complementary to the sequence bound to the polymer. Thus, the nucleic acid of interest would serve as a bridge to cross-link the polymeric molecules so as to set up a polymeric structure which would substantially slow the flow in the capillary and could, if desired, provide a plug.

Another exemplification would employ dual receptors, e.g., antibody to analyte and antibody to a particle, such as an antigen of a red blood cell (RBC). In quantitating a multivalent antigen, in the presence of antigen, cross linking would occur between the antigen, dual receptor and RBCs to form large complexes modulating the flow rate, while in the absence of the antigen no complexes would be formed. The assay could be carried out by combining the sample with RBCs before introducing the sample into the device or by providing RBCs in the sample receiving chamber. The reaction chamber would have the dual receptor where complex formation would be initiated.

For monovalent or haptenic analytes, the assay would be modified by employing a polyhapten reagent which could be added to the sample prior to introduction of the sample into the device. The presence of hapten would reduce complex formation in contrast to the result observed with the multivalent antigen analyte.

Any system which results in a change in flow velocity or can be coupled to a reagent or system which affects flow velocity may be measured. Various systems have already been indicated which result in changes in flow rate. Other systems which could be coupled to compounds of interest are light initiated catalysis of polymerization, cellular aggregation initiated by lectin cross-linking, enzymatic reactions resulting in polymer initiation in conjunction with water-soluble monomers, e.g., hydroxyalkyl acrylates, etc.

It is evident that the system permits a wide variety of variations which allows for a variety of protocols and reagents. Thus, any substance of interest which allows for flow in a capillary can be detected in accordance with the subject invention.

The flow in the capillary channel unit can be detected by various techniques which allow for detection of fluid flow, e.g., flow sensors or pressure sensors, or by having a detectable component in the assay medium, which can be detected visually or by diode assay. Techniques which allow for fluid flow determinations include the use of means for measuring triboelectricity, means for detecting the rate of passage of liquid, detecting Doppler effects, or the like. Preferably, a component is used in the medium which allows for flow detection by detecting the passage of the component through the first capillary channel exiting a receiving chamber.

Flow can be detected by the creation of a speckle pattern resulting from the movement of particles in the first capillary channel and the passage of a coherent light source, e.g., laser beam, or an LED, through the channel. (See, Powers et al., supra.)

A speckle pattern results from the interaction of particles and coherent light. Flow (motion) of the particles makes the speckels move with a frequency associated with the flow rate and the light or speckle fluctuations can be detected by a photodetector. The photodetector is designed to detect an area not greater than about the size of a speckle. A plurality of photodetector elements may be employed for detecting different areas and averaging the signals from each area. The speckle pattern can also be used to determine the size of the particles by analysis of the size of the speckles.

By employing a photodetector, the change in the light pattern as a result of a change in the rate of flow can be determined by appropriate electronic means, such as photodiodes or phototransistors, which would feed the electrical signal resulting from the fluctuating light to an appropriate circuit. Particularly easy to distinguish is a flowing liquid from a stationary liquid. Thus, the slowing or stoppage of flow can be readily detected and the change in rate of flow or the time of passage through the first capillary can be determined from the beginning of flow to the stoppage of flow.

One possible problem that can occur in capillary flow devices of the invention is depletion of blood or another sample from the reservoir prior to the stoppage of flow caused by the detectable event being measured, such as coagulation. When the liquid in the reservoir is drawn down so that essentially no more fluid is present in the reservoir, flow will stop since capillary forces will then be operating in both directions. Accordingly, it is useful to have a means of detecting this anomolous result in order to avoid a measurement of flow stoppage caused by this event being taken to represent the measurement flow stoppage.

Since the actual device containing the capillary channels and other chambers is typically a flat cartridge that is inserted into an instrument which makes the various electronic measurements, detection of reservoir depletion can be accomplished by embedding various sensors into the electronic device that holds the reaction cartridge.

Since the reservoir is generally external to the electronic device so that blood or another fluid can be applied directly to the reservoir, measurement of depletion of fluid in the reservoir typically takes place in the presence of ambient light and other ambient conditions, variation in which must be accounted for in any measurement technique. One suitable measurement technique is to apply modulated light to the reservoir in a region adjacent to the capillary leading to the reaction chambers and other parts of the apparatus. In fluids containing particles, such as red blood cells in blood, light is scattered in all directions through the fluid even though the light is applied perpendicular to the reservoir. Some light will be scattered down the entry capillary, which will then act as a light guide. However, the presence of particles in the fluid present in the capillary will again result in scattered light which passes out through the transparent walls of the light guide (capillary), where it can be measured by a photodetector. The capillary channel filled with blood can be considered to be a leaky waveguide for light, because a difference in refractive index between the blood (high refractive index) bounded by a low refractive index material (capillary channel) will provide light guidance, while the presence of red blood cells will scatter the light through the walls of the capillary channel, thereby providing the leaking effect. Since light will only be scattered in the presence of red blood cells or other particles, a detector located in close proximity to the channel will detect the scattered light. The modulation of the applied light will isolate the detector from ambient interferences. If the light is modulated at a defined frequency and detection electronics are sensitive only to that frequency, ambient effects will be eliminated. The modulation applied to the light can be of any type, such as sinusoidal waves or chopping, as long as the modulation can be both created and detected by electronic or mechanical means. Interferences from ambient light can further be eliminated by using infrared light, which offers additional advantages (when blood is the sample) of enhanced scattering and transmission.

This technique for detecting depletion of fluid in the reservoir offers several advantages over other techniques. Detection of fluids in capillary channels is normally accomplished by measuring changes in absorption or transmission of light passed through the channel. However, in certain instances this will not be possible because of the physical restrictions on the reservoir and its location in the capillary device and the electronic apparatus into which the capillary device is inserted. For example, the size of a finger, if blood is being obtained from a finger stick, will require that the reservoir be separated sufficiently from the electronic device to allow the finger to be placed onto the reservoir. This will mean that both sides of the capillary device adjacent to the reservoir are not in contact with the electronic apparatus since at least one side must be accessible for the finger.

With the method discussed here, there is no need to have both sides of the capillary available for transmission and detection of light. Because a scattering effect is used, the detector can be present either on the same side of the capillary on which light is applied, on the opposite side, or in any other physical relation as long as the detector is located adjacent to the channel.

An additional useful control device is some means for simulating blood flow through a capillary channel in order to determine whether the electronic apparatus into which the cartridge is being inserted is fully operational. Numerous means of accomplishing this result are available, but one useful technique not believed to be previously used in any similar manner is described below.

As described previously, one useful technique for measuring blood flow is to detect the presence of the speckled pattern that results from the interaction of particles and coherent light. Any technique that simulates blood flow when such a detection system is being used will need to simulate the speckled pattern of light. Since the detector and the coherent light source are typically located in a close spatial relationship directly opposite each other so that insertion of the capillary device will result in light from the coherent light source passing directly through a channel in the device to the detector, simulation of blood flow requires insertion of some device into the electronic apparatus that can modulate the light beam. While this could be accomplished using a second device that could, for example, produce modulated light, a useful technique is to include electronics and modulating devices directly in the capillary device so that each capillary cartridge can be used to determine the operating characteristics of the electronic apparatus containing the coherent light source and detector immediately prior to actual measurement being taken. However, this requires that the speckled pattern generator be such that it will not then interfere with the actual measurement. One means of accomplishing these results is to include a liquid crystal display-type apparatus at the location where measurement is being made. The liquid crystal material is selected so as to rotate polarized light that passes through it, the typical means by which liquid crystals operate. Polarizer filters will be present, either in the cartridge itself or in the electronic apparatus into which the cartridge is inserted that will result in the passage of light through the polarizing filters when the liquid crystal device is turned off. However, when the liquid crystal device is activated by application of a voltage, light passage will be blocked.

Typically, when the liquid crystal device is activated, it rotates the polarization of the laser beam, thereby reducing the passage of a light and generating light amplitude fluctuations, which are detected as being equivalent to the moving speckled pattern generated by passing coherent light through the thin film of particle-containing fluid that would normally flow down the capillary channel.

A low viscosity liquid crystal material having a high refractive index change (thereby enabling rapid fluctuations) is desirable. A typical design uses a crystal oscillator and a chain of binary counters from which the liquid crystal display driver signals are derived as well as the time base for the measurements to be taken.

In order to further consideration of the invention, a number of illustrative devices which may be used will now be considered. As already indicated, the device will have at least one capillary channel unit, one chamber unit, an entry port, a vent, and a reagent bound to the surface.

The device will be fabricated from materials with the appropriate physical properties, such as optical transmission, thermal conductivity, and mechanical properties, and which allow for uniform coating and stability of reagent, as well as medium compatibility, for example, blood compatibility. Where blood is the medium, the material should be configured to assure good blood flow stoppage or slowing once clotting is initiated. For this purpose, suitable plastics include those for high surface free energies and low water sorption, including PETG (polyethylene terephthalate glycol), polyester (Mylar ®), polycarbonate (Lexan ®), polyvinyl chloride, polystyrene, and SAN (styrene-acrylonitrile). A particularly preferred plastic is acrylonitrile-butadiene-styrene (ABS), particularly ABS supplied by Borg Warner under the tradename Cycolac. However, since these plastics are hydrophobic and exhibit poor reagent coating and poor blood flow, the plastics can be rendered hydrophilic by treatment with argon plasma, using a plasma etcher or corona discharge. Suitable conditions are 10–25 watts at 13.56 MHz and one torr chamber pressure for 5–10 min. Alternatively, a protein, e.g., albumin coating, can be used in some instances by passing a solution through the device having from about 1–5% serum albumin, allowing the solution to stand for 30 min., wiping and drying. Other modifications may also find application. Plasma etching and corona discharge provide markedly superior flow control characteristics and reproducibility.

The device can be fabricated in a variety of ways. The receiving and reaction chambers can be formed in the plastic sheed by vacuum forming (PETG), injection molding (PETG, polystyrene, SAN), or hot stamping. Capillaries may be formed by etching a channel into the plastic. The device can be sealed by placing a cover slip (with appropriate vent holes at the inlet and vent) on the base sheet, and sealing with ultrasonic welding or by solvent bonding. Of these techniques, markedly superior products are obtained by injection molding of the plastic device in pieces so as to form a depression in at least one surface of at least one plastic piece. ABS polymers are particularly suited to injection molding and additionally provide a clear plastic which is suitable for numerous optical detection techniques. ABS polymers are also suitable for ultrasonic welding. It is preferred to form the chambers from two substantially flat plastic pieces in which the capillaries and other chambers are formed by producing matching depressions in two surfaces of two different shaped plastic pieces. It is preferred that on one of the pieces ridges, known as energy directors, completely surround the depression in a closely spaced relation so as to form a surface of first contact when the two pieces are placed together. When ABS is used, the ridges are typically 7.5 mil ±0.5 mil above the surface of the plastic. The ridges are typically formed in the shape of a triangle, typically an equilateral triangle. The center of the ridge is typically 17.5 ±0.5 mils from the edge of the depression that will form the chamber. Use of such energy directors with ultrasonic welding produces a highly reproducible seal around the edges of the internal chamber that is formed when the two sheets are ultrasonically welded together. Access ports are typically formed by molding or drilling holes into the depressed surfaces of the individual plastic pieces prior to welding. Accordingly, the welded ridges form a complete seal around the lateral edges of the internal chambers.

Alternatively, the pattern can be dye cut in a double-sided adhesive tape (e.g., 3 M No. 666 tape, Fasson Fastape A) of appropriate thickness which is then sandwiched between a plastic base and cover slide. Or, the sandwiched layer may be die cut from a plastic piece of appropriate thickness which would be coated with adhesive and sandwiched in the same manner as the tape. The adhesive could also be silk-screened onto the base to give a raised pattern of desired thickness.

The sheet thickness of the device in the region of the capillary channels will generally be equal to or exceed about 2 mil to prevent compression due to the capillary action. In the embodiment involving the sandwich, each of the plastic layers comprising the top and bottom will be at least about 10 mil thick.

While other materials may be used for fabrication, such as glass, for the most part these materials lack one or more of the desirable characteristics of the indicated materials and therefore have not been discussed. However, there may be particular situations where glass, ceramic or other material may find application, such as a glass window for optical clarity, modification of surface tension, and the like.

The device will normally include a reagent within the reaction chamber. In formulating the reagent(s), it may be formulated neat or with various additives. The manner in which it is formulated, introduced into the reaction chamber and maintained in the reaction chamber, must provide for rapid mixing with the sample, reproducible distribution in the chamber, stability during storage, and reproducible reaction with the sample.

In order to assure the reproducibility of distribution, various techniques may be employed for introducing the reagent into the chamber. Where the device is produced as two parts which fit together, the reagent may be sprayed, painted, introduced into the chamber as a liquid, lyophilized or evaporated, adsorbed, covalently conjugated, or the like. The active reagent may be combined with various stabilizers, excipients, buffers or other additives involved with the reaction. Alternatively, a small vial or other holder may be attached to the reaction unit, usually chamber, being stored as a liquid, where the liquid may be introduced into the reaction unit prior or concurrently with the sample entry into the reaction unit. A second receiving chamber may be employed connected to the reaction unit by a capillary channel, where transfer of the reagent in the second receiving chamber to the reaction unit is initiated in relation to introduction of the sample. For example, the second receiving chamber could be filled and sealed, and then unsealed when the sample is introduced into the sample receiving unit.

To enhance mixing, various mechanical or ultrasonic means may be employed to agitate the sample and reagents, where the mixing means may be internal or external. Vibrators, ultrasonic transducers, magnetic rods or other mechanical mixing means, flow disrupters, mixing baffles or barriers, flow directors, or the like, may be employed. The particular manner in which agitation is provided, if provided, will vary widely depending upon the degree of agitation needed, the design of the device, and the like.

Various chemicals can be used to ehance dissolution in a uniform manner. Such chemicals may include surfactants, polyols, sugars, emollients, liquids, or the like. Depending upon the nature of the reagents, the reagents may be formulated in a variety of ways to insure rapid and uniform mixing.

Other chemicals can also be present in the reagent chambers. For example, if the device is being used to measure prothrombin time and a control sample containing heparin is being used, such as described in an application filed on even date with the present application (Ser. No. 880,696) and entitled "Whole Blood Control", which is herein incorporated by reference, said application being assigned to the same assignee as the present application, a heparin antagonist can be used to eliminate the effects of heparin on prothrombin time measurement. Typical heparin antagonists include protamine sulfate and polybrene.

The reagent need not be coated or bound to the surface of the device, but may be provided as a soluble sponge or gel or alternatively, absorbed onto an insoluble sponge, membrane, paper (e.g., filter paper) or gel which is introduced into the reaction unit. In this manner the fluid may pass through the foam structure dissolving the reagent so as to form the reaction mixture.

The reagent may be provided in liquid form in microcapsules. The liquid reagent could be released from the microcapsules by applying pressure to the walls of the reaction unit, resulting in breaking of the microcapsules and releasing the liquid reagent.

Also, as already indicated, the reagent need not be limited to a single reaction unit. The same or different reagents may be introduced into the capillary or in successive reaction units. In this manner a cascading reaction may be performed, where one is interested in allowing each reaction step of a sequence to proceed for a predetermined period before encountering the next reagent. Multiple reaction units also allow for the removal of components in the sample which may interfere with the desired reaction. By having receptors in the first units, one or more endogenous components may be removed. Where particles are to be removed, filters may be employed at the entrance or exit to a reaction unit.

In addition to the chemical reagent, microparticles may be also included in the reaction unit which would be entrained with the moving front, where the microparticles could aid in the plug-forming mechanism for flow stoppage.

In performing the assay, a sample would be taken and treated as may be appropriate. Blood for example might be diluted and various reagents added, particularly where there is an interest in the determination of a particular clotting or anti-clotting factor. In specific binding assays, various particles might be added which had been functionalized by the addition of specific binding members, such as haptens, ligands, and receptors, particularly antibodies. In some instances, the system may be devised where clotting will occur in the absence of the analyte. Thus, reagents will be added which, in the absence of the analyte, would be degraded in the reaction chamber.

Once the various materials are mixed to form the sample medium, the sample medium would be introduced into the receiving unit and transferred by capillary action into the next unit. Either visual evaluation of the flow rate change or an electro-mechanical evaluation may be employed. The initiation of flow through the first capillary channel or through a successive capillary channel may be selected as the initiation time for measurement, or some point in between. As already indicated, various means may be employed for determining the flow velocity or time to flow stoppage.

For measuring a speckle pattern, which is obtained with particles, as are present in blood, an apparatus comprising a semiconductor laser and photodectors may be employed. By exposing a photodetector of sufficiently small area to a speckle pattern, a random signal (noise) is observed. The average of the random signal observed as a DC signal is inversely proportional to the red cell density, and changes in the fluctuation continues until flow stoppage, e.g., clotting, occurs. Such apparatus may include a housing for receiving and holding the device and means for controlling the temperature.

The size of the area which is detected by an individual photodetector may be controlled in a variety of ways. One way, as indicated above, is to use a photodetector which has only a small photosensitive area, up to about the size of the speckle spot. Another way is to use an optical fiber. By controlling the parameters of the fiber, the area from which the fiber receives light may be controlled. Instead of a fiber, lenses may be employed to limit the observed area which lenses may be separate from or molded into the device.

Where other than flow stoppage is involved, various spectrophotomers, fluorimeters, or the like, may be employed for detection of the detectable signal. Depending upon the nature of the assay protocol, a single determination or multiple determinations may be made, based on a fixed value or a kinetic determination.

Figure 1B:
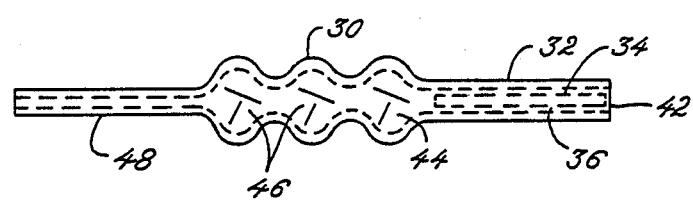

Various devices may be devised for the subject assays. In FIGS. 1A and 1B devices are depicted involving single chambers and one or two capillary units. These devices can be fabricated in a variety of ways, for example, having two sheets, where each of the sheets have been molded so as to define the particular units or one of the sheets defines the units and the other is a cover sheet, or having three sheets, where a sheet having cutouts defining the units is sandwiched between the other two sheets, where one or the other sheets provides the necessary orifices for the various ports. Other techniques may also be found to be useful for providing the chamber and channel cavities.

In employing device 10 of FIG. 1A, capillary 12 is introduced into the sample, so that the inlet port 14 is completely submerged in the sample. It is important to avoid any air bubbles where the air bubbles could interfere with the measurement. The inner surface of the upper portion of capillary 12 is coated with a reagent, (not shown) so that as the liquid sample transits the capillary 12, the reagent becomes dissolved in the sample. When the liquid front reaches index 18, the capillary is removed from the sample, defining the sample volume, and the capillary inserted into a second fluid to maintain continuous flow. Otherwise, the sample drop can maintain a reservoir outside of the inlet port 14. The sample flows through capillary 12 into chamber 20 having vent 22. A second reagent is coated onto the inner surface of reaction chamber 20, where the assay medium undergoes a second reaction.

In using this device, an assay medium could be prepared as the sample involving the fluid suspected of containing the analyte and a buffered mixture of enzyme-analyte conjugate. The reagent in capillary 12 would be antibody to the analyte, so that the enzyme-analyte conjugate present in the assay medium would become bound to the antibody in an amount related to the amount of analyte in the assay medium. The assay medium would then enter the chamber 20, where the reagent would be substrate for the enzyme. One can employ a substrate of limited solubility, so that the amount of substrate rapidly reaches equilibrium and remains constant during the measurment. One can also have a high concentration of a soluble substrate to maintain substrate concentration constant during the measurement. One can then determine the rate of formation of product which will be dependent upon the amount of active enzyme present in the chamber. Since the amount of active enzyme can be related to the amount of analyte, this rate will therefore be proportional to the amount of analyte in the sample. By employing a substrate and enzyme which produces a colored or fluorescent product, the rate can be monitored by the change in color or change in fluorescence over a predetermined time period.

In FIG. 1B, device 30 has capillary 32 which is divided into channels 34 and 36 containing different reagents (not shown). The two channels share a common inlet port 42. Channel 34 contains a reagent, referred to as the first channel and the first reagent, which could be microparticles to which are conjugated antibodies to a first epitope. Channel 36 and its reagent, referred to as the second channel and the second reagent, would contain microparticles having monoclonal antibodies to a second epitope. In each case, the amount of monoclonal antibody would be substantial excess of any analyte which would be encountered. The analyte of interest would have a single epitope binding to the first reagent and a single epitope binding to the second reagent. The sample would travel through the channels at a substantially constant rate, with reaction occurring with any substance having the appropriate epitope.

All of the components present in the assay medium having the appropriate epitopes would react with the particle conjugates and become bound to the particle conjugates. The particle conjugates would then exit channels 34 and 36 and enter incubation chamber 44. The chamber would also provide for capillary action, and agitation due to its accordian shape and vanes 46 for causing turbulence in the chamber 44. Thus, as the assay medium exited the channels 34 and 36, the microparticles would mix and cross link, if any analyte was present which had the two epitopes on the same molecule.

In the incubation chamber, the particles would have sufficient time to aggregate, so that upon entry into exit capillary 48, the particles which are formed would have a significant effect on the flow rate in capillary 48. By measuring the rate of flow or determining particle size or number of particles in capillary 48, one could determine the presence and amount of an analyte having both epitopes. The rate of flow or other parameter could be determined by the rate at which particles above a certain size transited a light path, using minimum light intensity fluctuations, level of scatter, or the like.

The subject device illustrates the opportunity for having a plurality of capillaries to divide a sample into a plurality or portions, where each of the portions can be treated differently. The differently treated portions may then be brought together into a single chamber, where the different portions may interact in accordance with the desired protocol. Depending upon the nature of the protocol, the resulting assay medium may then be transferred to a capillary which may provide for measurement or may be further transferred to additional chambers for further modification.

Figure 2A:
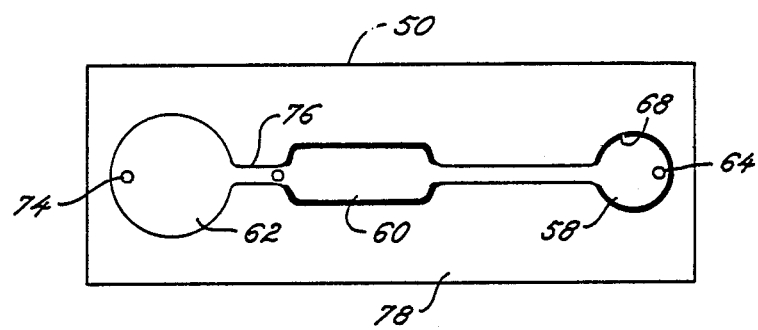
FIGS. 2A and 2B are a plan view and a side elevational view of a device employing three chambers.
Figure 2B:
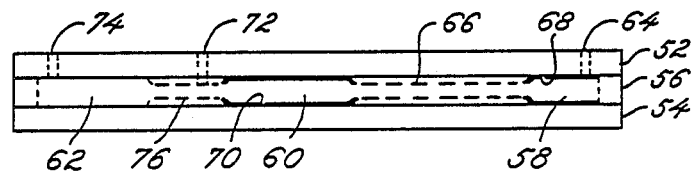

In FIGS. 2A and 2B are depicted a device having a plurality of chambers and allowing for interrupted flow. The device 50 is fabricated from three sheets, an upper sheet 52, a lower sheet 54, and a spacing sheet 56, which defines the various capillary units and chamber units. The device has three chambers, the receiving chamber 58, the reaction chamber 60, and the effluent chamber 62. Inlet port 64 receives the sample which is measured by filling chamber 58 and reaching the first capillary 66. Receiving chamber 58 is coated with first reagent 68, so that the sample undergoes a reaction in receiving chamber 58 and is modified.

The modified sample then passes through capillary 66 and enters reaction chamber 60, which is coated with second reagent 70. The second reagent, like the first reagent, is part of a detection system to provide for a detectable signal. Vent 72 is provided to stop the flow and allow for incubation in reaction chamber 60. This can be particularly useful where the slow step in the development of the detection system is complex formation. Depending upon the nature of the protocol, the period of incubation may be specifically timed incubation or may be one which is allowed to sit for a sufficient time to ensure completion and then the determination made. Effluent chamber 62 has exit vent 74 to permit flow past intermediate vent 72 when intermediate vent 72 is closed. Upon closing of intermediate vent 72, the assay medium will then flow through capillary 76 into effluent chamber 62. Instead of sealing the vent, other alternatives, such as applying pressure or centrifugal force, may be used to restart flow.

The device is comprised of a block 78 which may be configured to be introduced into a instrument for assay determination. As already indicated, the various sheets will be constructed so as to ensure sufficient mechanical stability to withstand capillary action and provide for the necessary characteristics for flow of the assay medium and detection of the detectable signal.

The subject device may be employed for flow stoppage, such as coagulation, where the coagulation may occur in the effluent chamber 62. One could measure the rate of flow in capillary 66 or determine the time of flow stoppage, particularly where capillary 76 is elongated (See FIG. 5) and a plug forms in capillary 76.

In this device, one could provide for a determination of particle count, where the first chamber has bead conjugated ligands and the analyte of interest is a particular antibody. The sample would be introduced into the receiving chamber 58, where reaction would occur between the bead conjugated ligands and any antibody present in the sample. The sample would then flow to the reaction chamber 60, which would contain a reagent which binds specifically to antibody-ligand complexes, such as *S. aureus* protein A or rheumatoid factor, which binds specifically to poly(antibody-ligand) complexes. Thus, any bead conjugate which becomes bound to antibody, would be removed from the liquid phase of the assay medium. The device 50 could then be inserted into an instrument, which would cover vent 72, allowing for flow through capillary 76. One could then determine the number of particles or beads in the assay medium in the chamber 62 or capillary 76 as a measure of the amount of antibody in the sample.

Alternatively, one could provide for complex formation between Fab fragments and major histocompatibility antigens of cells in the receiving chamber 58. Thus, reagent 68 would be Fab fragments of monoclonal antibodies specific for the major histocompatibility antigen. The Fab fragments could be from murine or other non-human source of monoclonal antibodies. The reagent 70 would then be particles to which anti-murine immunoglobulin were conjugated. In this way, when the Fab-bound cells entered the reaction chamber 60, they would bind to the latex particle conjugates so as to form extended structures. Upon closing of the vent 72 by introducing device 50 into an instrument, the medium would flow through capillary 76, where large particles could be determined by the scattering of light, or the pattern of transmission of light through the capillary and blockage by the cellular-particle aggregations.

Figure 3:
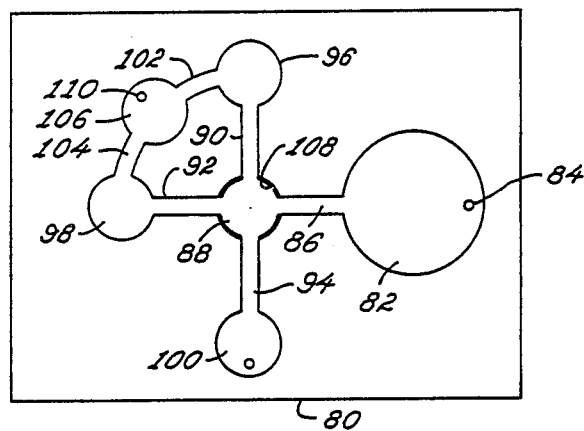
FIG. 3 is a plan view of a device for a plurality of simultaneous determinations.

In FIG. 3 is depicted a device which is exemplary of the determination of a plurality of anlaytes in a single sample. The device 80 has a receiving chamber 82 with inlet port 84.

The sample would be introduced into the receiving chamber 82 and be pumped by capillary action through channel 86 into reaction chamber 88. In reaction chamber 88 would be one or more reagents 108 which would provide part of the detection system. From reaction chamber 88, the assay medium would then be pumped by means of capillaries 90, 92 and 94 to chambers 96, 98 and 100, respectively. The media in chambers 96 and 98 would then be pumped by means of side capillaries 102 and 104 to final chamber 106. In this way, a variety of reactions could occur, where reagents could be provided in the various side chambers for further reaction allowing for detection of a plurality of epitopic sites.

An illustrative of the above apparatus, one could determine from a lysate, the serotype of a particular pathogen. The lysate would be introduced through inlet port 84 into the receiving chamber 82 and then be pumped into the reaction chamber 88. In the reaction chamber 88 would be reagent 108 which would be monoclonal antibody-bead conjugates to a public epitope of the particular pathogen. One would then measure the particle count in capillaries 90, 92 and 94, which would provide the base line for the particle count which should be present in chamber 96, 98 and 100. In each of the chambers 96, 98 and 100, would be monoclonal antibodies to an epitope specific for a particular serotype, where the antibodies are conjugated to larger beads which are distinguishable by light scattering properties from the beads in chamber 108. Thus, if the signal character changes in chambers 96, 98 or 100, this would be indicative of the particular serotype.

If one wished to determine if the serotype had another antigen of interest, one could provide for antibodies to the particular antigen in chamber 106. Chamber 106, a narrow chamber susceptible to particle blockage, would have vent 110 to allow for flow into chamber 106. Capillaries 102 and 104 would pump the assay medium from chambers 96 and 98 into chamber 106, where the presence of the particular antigen would result in cross linking of the antigen. Cross-linking of the antigen would result in plug formation.

Other combinations of labels and protocols may be employed. By dividing the assay medium into multiple pathways, the assay medium can be treated in multiple different ways and, if desired, rejoined in a single chamber as indicated above. This can be useful in situations where one is interested in different analytes, which may have different combinations of epitopes, or where the analyte must be treated in different ways in order to provide the detectable signal, or where one wished to add different combinations of labels to the analyte, where one wishes to provide a check on the results observed, or the like.

Figure 4:
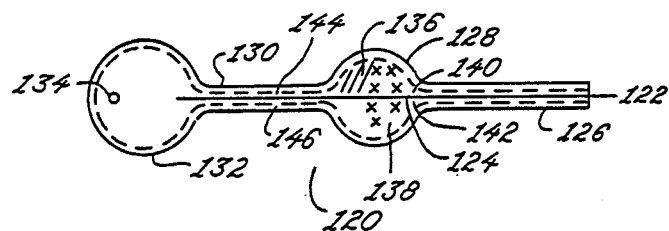
FIG. 4 is a plan view of an alternate embodiment, where the sample is divided into two separate channels.

In FIG. 4 is depicted a device which allows for the simultaneous determination of a sample background value and the detectable signal. The device 120 has an inlet port 122 separated by partition 124 which extends through capillary 126, chamber 128 and second capillary 130. Capillary 130 evacuates into effluent chamber 132 having vent 134. Chamber 128 is divided into two half chambers or semichambers 136 and 138. In semichamber 136, two reagents are present indicated by the slanted lines and the crosses. The slanted lines are monoclonal antibodies specific for an epitope on the analyte, where the antibodies are nondiffusively bound to the surface. The crosses indicate monoclonal antibodies conjugated to fluorescers, where the monoclonal antibodies bind to a different epitope of the analyte. The fluorescer conjugate is reversibly bound to the surface of the two chambers 136 and 138 in the area near the entry ports 140 and 142 of capillary 126.

In carrying out the assay, the sample inlet port is submerged into the sample and the sample allowed to rise in the capillary 126. Sufficient sample is introduced and the two chambers 136 and 138 are filled.

As the sample transits the two semichambers, different events will occur. In the sample reaction chamber any analyte will become bound both to thee antibody bound to the surface and the fluorescer conjugate, so that the amount of fluorescer conjugate which remains in the sample reaction chamber 136 will be dependent upon the amount of analyte in the sample. By contrast, sample which traverses control reaction chamber 138 will bind to the fluorescer conjugate but continue through the chamber into capillary 130.

By appropriate optics, one can read the fluorescence from the two capillary regions 144 and 146. The capillary region 144 will be the region for determination of the amount of analyte, while the capillary region 146 will serve as the control. Thus, the amount of fluorescence observed in region 146 will be the maximum amount of fluorescence available from the combination of sample and fluorescer conjugate. Any reduction in fluorescence in the capillary region 144 will be as a direct result of the presence of analyte. The two streams will then exit into effluent chamber 132.

Figure 5:
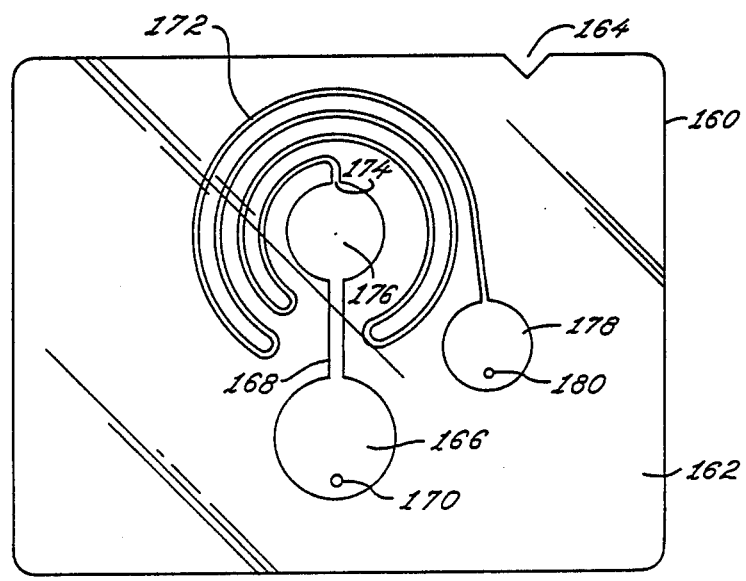
FIG. 5 is a plan view of an alternate embodiment employing an extended capillary path.

As shown in FIG. 5, the next embodiment 160 provides a serpentine path. The device has a housing 162 which is a rectangular plastic block shaped to fit into a reading apparatus (not shown). The block is indexed at site 164 for alignment to the apparatus. The receiving chamber 166 has a volume about one and one-half times the volume of the reaction chamber. The two chambers are connected by the first capillary channel 168. Inlet port 170 provides for introduction of the assay sample by syringe, eyedropper, or other convenient means. A serpentine capillary path 172 connects to outlet 174 of reaction chamber 176. The serpentine channel 172 terminates in reservoir chamber 178 which has outlet port 180.

Various other configurations can be employed in particular situations. For example, one could employ a "Y"-shaped device where one arm of the Y has a sample receiving chamber with the inlet port sealed. The sample receiving chamber is connected through a first conduit to the mixing member which serves as the trunk of the Y. The first conduit may be filled with a fluid which may be a buffer solution or other diluent.

The second arm of the Y has a fluid chamber with a removable seal over a port. The fluid chamber is filled with a fluid which may serve as a diluent, reagent source, or the like. The fluid chamber may be as large as desired so that it may provide the desired ratio of fluid to sample. The fluid chamber is connected to the mixing member through a second conduit which is also filled with the fluid of the fluid chamber. The cross-sections of the first and second conduits are selected to provide for the proper volume ratio of the fluid and sample.

The mixing member may be a capillary or chamber. The mixing member may be the final element of the device or may be connected to additional elements. Thus, the Y can serve as a complete device, by providing the mixing member with an outlet port or a part of a larger device by connecting the mixing member to additional capillaries and/or chambers.

To use the Y, the seals are removed from the fluid chamber and sample chamber, while retaining the outlet port sealed to prevent flow. The inlet port may then be contacted with the sample and the outlet port unsealed. The sample and fluid from the two chambers will begin to flow and be mixed in the mixing member in the proper proportion. Depending on the particular protocol, one can determine a number of different events by reading the flow of fluid in one of the capillaries.

One application would be to provide fluorescent antibodies in the fluid chamber. Where the sample contains cells having the homologous ligand the mixing of the fluorescent antibodies and cells will result in large fluorescent particles as a result of the homologous antigen being present on the cells. These large fluorescent particles could then be detected by various means.

Figure 6A:
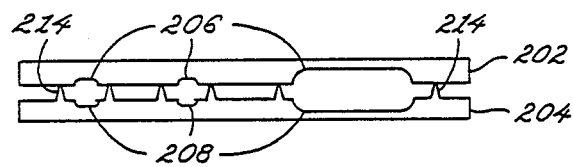
FIGS. 6A and 6B are a cross-sectional view of an embodiment showing the location of channels and energy directing ridges during the fabrication process.

FIG. 6A shows a cross-sectional view through a section of a hypothetical device being prepared by ultrasonic welding from two injection-molded plastic pieces (not necessarily shown in any of the previous figures), prior to ultrasonic welding. The two plastic pieces 202 and 204 that will be used to form the internal chambers are shown properly aligned (i.e., in register) in FIG. 6A. "Registration" is used here in the printing sense, referring to proper alignment of the depressions present in the surfaces of the two pieces that are used to form the internal chambers and capillaries. Proper registration can be aided by injection molding the two pieces to provide projections on one piece that fit into holes or depressions (other than capillary- or chamber-forming depressions) in the second piece. A single convoluted depression, 206 and 208, respectively, is formed into the surface of each piece, but the cross-sectional view shown in the figure cuts through the depression at three separate locations, two of which will result in capillary spaces (210 in FIG. 6B) while the remaining location will result in the formation of a larger reaction chamber (212 in FIG. 6B). Energy-directing ridges 214 can be seen in the surface of one of the two plastic pieces (204) adjacent to the periphery of the depression.

Figure 6B:
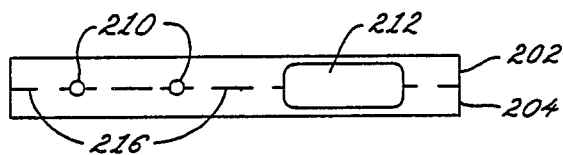

FIG. 6B shows the same cross-sectional view after ultrasonic welding. The plastic has melted selectively in the region of the energy-directing ridges so that the two plastic pieces have melted into each other to form a seal around the capillary and the reaction chamber. In order to minimize the destructive effects of heat caused by the ultrasonic welding, ultrasonic welding is carried out only until a seal is formed and does not need to be carried out until the entire plastic surfaces have welded together. Unwelded contact surfaces are shown by reference numbers 216 in FIG. 6B. Use of energy ridges and short welding times also ensure that the dimensions of the depressions will be unaffected by the welding event. Welding time will be selected so that the melting (welding) almost but not quite reaches the edge of the depression. The extremely small cracks left between the two plates in the area of the capillaries will not adversely effect capillary action.

Figure 7:
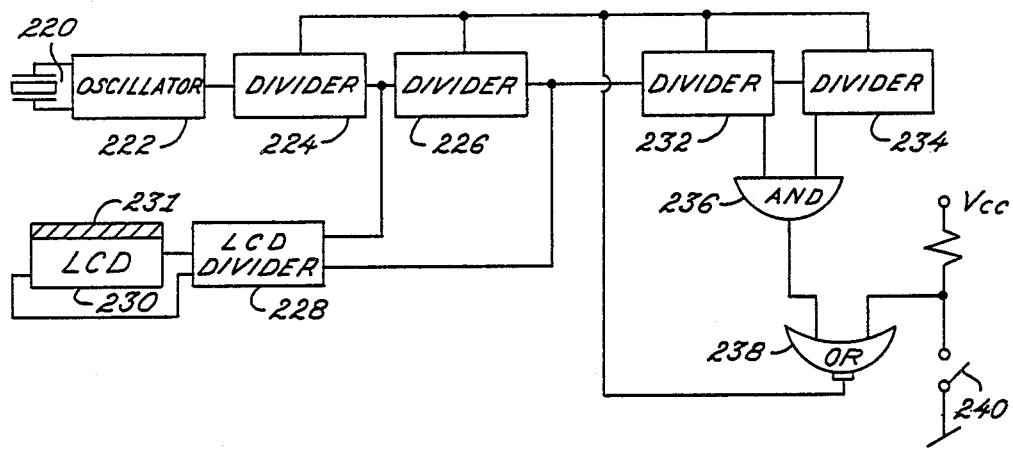
FIG. 7 is a block diagram of an electronic circuit suitable for use in an electronic capillary cartridge device to simulate the passage of blood through a capillary in a control cycle.

FIG. 7 shows electronic circuitry that can be utilized to simulate the passage of blood through a capillary flow device. The circuitry includes a crystal-controlled oscillator in which 220 represents the crystal and 222 represents the oscillator. The signal from the oscillator drives two frequency dividers (224 and 226) that will generate the output signals for a driver 228 of a liquid crystal display cell 230. Cell 230 is biased by an oscillating signal having a specific rate of oscillation, for example 128 Hz. The cell will therefore rotate its polarization at the rate of 128 Hz. Polarizer 231 in combination with cell 230 therefore operate to alternately block and pass light as a result of the rotating polarization.

Two more dividers (232 and 234) drive a logical AND gate (236) whose output will go to a logic circuit low at defined intervals, for example, approximately every 20 seconds. When the output goes to a logical low, the output of a logical OR gate (238) will reset the dividers, thereby stopping the process. Accordingly, modulating signals for the liquid crystal display cell 230 are generated for the set time period, 20 seconds in the above example.

The device is provided with a start switch 240. When switch 240 is closed, the reset signal is cleared, and the process is restarted.

The oscillator, dividers, logic gates, and liquid crystal display driver can be implemented in CMOS (complementary metal oxide semiconductor) technology using standard techniques of electronic fabrication. An CMOS device can be readily powered through more than 10,000 cycles when powered by a cointype lithium battery.

Figure 8:
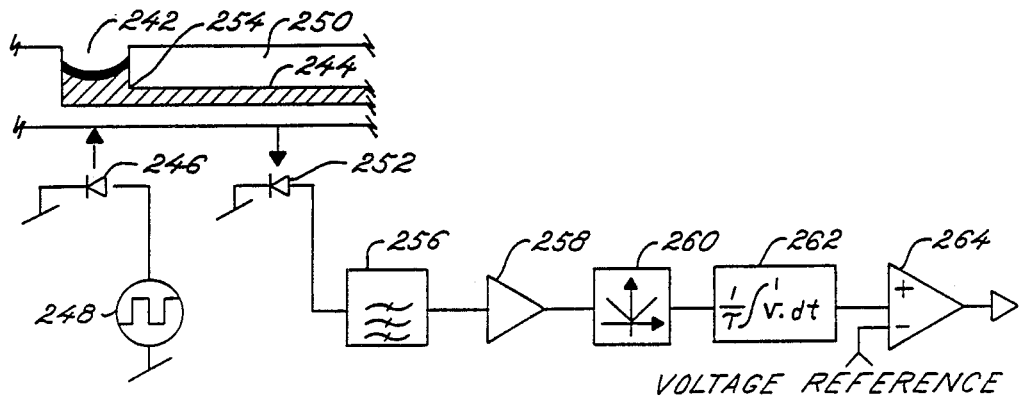
FIG. 8 is a diagram of the physical location and electronic circuitry of a detector capable of determining depletion of sample in a reservoir of a capillary device.

FIG. 8 shows a device for determining when the sample present in a reservoir is depleted. In this figure, blood is presumed to be the sample. When blood is applied to sample reservoir 242 it will start flowing immediately down capillary channel 244 by capillary action. A light source 246, typically an infrared light-emitting-diode (LED), is located adjacent to the blood reservoir near the capillary entrance. Light source 246 is modulated by a modulator 248, typically a sinusoidal wave or square wave generator. A typical modulation frequency is about 8 KHz. The modulated light will be scattered by red blood cells in the blood sample, and a fraction of this light will be guided by capillary channel 244 formed in the plastic capillary flow device 250. Since the red blood cells in the sample will further scatter this guided light, photodetector 252, typically located in close proximity to the inlet 254 of the capillary channel, will capture some of the scattered light. The signal output of the photodetector will consist of the superposition of ambient light and scattered light. The scattered light component is separated from the ambient light by a band-pass filter 256 and is further amplified by amplifer 258. This signal is rectified by rectifier 260 and integrated by integrater 262 in order to generate a direct current voltage proportional to the scattered light. Other types of signal generators can be used to produce a detectable signal that is seperable from ambient light and its possible variations. Examples include wave lengths (e.g., use of infrared light sources), light pulses, sinusoidal wave generation, and digital encodation. When methods other than frequency modulation are used to produce the detectable signal, the term "filter" as used in this specification refers to any means of separating the detectable signal from variation in ambient light.

Although the exact location of the ambient light source and detector in relation to the junction between the blood reservoir and the capillary can be varied depending on the capillary size, strength of a light source, detection limit of the detector, adsorbance of the sample, and the like, it is preferred that both the light source and the detector by relatively close to the junction, particularly when a highly abosrbant sample such as blood, it is utilized. When an infrared light source is used, it is preferred to place the light source from 0.5 to 2 mm from the capillary entrance with an infrared-sensitive photodetector being located from 1 to 4 mm from the junction.

As the blood reservoir empties due to the capillary flow, the light path between light source 246 and photodetector 252 will be interrupted, thereby reducing the voltage output from integrator 262. By connecting the output of the integration to a comparator 264, a logical level indicating the presence or absence of sample in the reservoir is obtained. Furthermore, by adjusting the position of the light source or the reference voltage of the comparator, the volume of sample in the reservoir at which the decision "no sample" is made can be controlled.

An infrared light source is preferred because of its larger efficiency in converting electric current into light, as compared to visible-light light-emitting-diodes. A modulating frequency of several kilohertz (preferably 3 to 20 kHz) is selected in order the remove the modulation frequency from the low 60 Hz harmonics present in artificial illumination, thereby simplifying the separation of ambient light and signal light. The separation is enhanced even further by the selection of an infrared light source.

Obviously, various designs of the individual chambers and channels can be provided. The designs and channels will be selected to provide for optimum sensitivity for particular assays. The volumes of the chambers will be chosen so as to accommodate an appropriate sample volume. The nature and cross section of the first capillary channel together with the size of the reaction chamber will control the residence time of the assay medium in the reaction chamber. In some systems a reaction will terminate upon the sample exiting the reaction chamber, e.g., antigen-antibody complex formation, pro-enzyme to enzyme, etc., where a component is bound to the surface of the chamber. The reaction occurring in the reaction chamber, may result in a product which produces a blockage in the second capillarly channel or prevents a blockage from forming. The residence time for the reaction in the reaction chamber can be carefully controlled by controlling the dimensions of the capillary channels and reaction chamber, as well as temperature.

It is evident that any type of capillary channel may be employed which provides for accommodating the appropriate volume and time period to flow stoppage. Various designs may be used such as serpentine, linear, U-shaped, pleated, or the like. The channel cross-section may be circular, ellipsoid, rectangular, or combinations thereof. The length of the channels may be determined empirically depending upon the other parameters involved.

The initial or metering channel may be of constant or varying cross-section. With a constant cross-section, the observed flow velocity will diminish with the path length traversed. Therefore, the observed change in velocity will have two components: (1) an inherent reduction in velocity related to the increasing friction with increasing fluid path length; and (2) increasing or decreasing viscosity of the medium due to any reaction occurring.

In order to eliminate the effect of the fluid path length, a tapered capillary may be employed. The taper can be calculated by determining the cross-section, e.g., height and width, of the channel for each point along the channel path. The equations below are employed. The equations are based on known principles of fluid mechanics (e.g., R. Byron Bird, Warren E. Stewart, Edwin N. Lightfoot, *Transport Phenomena*, John Wiley & Sons, Inc., 1960).

The flowrate, Q, measured by the laser (in the first capillary channel) can be defined by:

$$Q = VA = \frac{\pi r^4}{8\mu} \cdot \frac{\Delta P}{z} \quad (1)$$

where, V is the velocity in the 2nd capillary, and A is the area of the 1st capillary channel, and:

r = radius of the 2nd capillary channel
$\mu$ = viscosity of the fluid
z = distance down the 2nd capillary channel
$\Delta P$ = the pressure drop in the 2nd capillary is defined by:

$$\Delta P = \frac{2\gamma \cdot \cos\phi}{r} \quad (2)$$

wherein:
$\gamma$ = surface tension of the fluid
$\phi$ = contact angle of fluid with surface Combining (1) and (2), the flowrate, Q, becomes:

$$Q = \frac{\gamma r^3 \pi \cdot \cos\phi}{4z\mu} \quad (3)$$

Form (3) it can be seen that the radius of the 2nd capillary channel is proportional to the distance down the channel, z:

$$r = kz^{\frac{1}{3}} \text{ where } k = \frac{4Q^*\mu}{\gamma\pi \cdot \cos\phi}$$

and and Q* is the desired constant flowrate in the 2nd capillary channel. Using the above equations and selecting a desired Q*, the following table indicates the changes in radius at the position defined by z, for k=0.034

| Length mm | Radius mm | Flowrate mm³/sec | Inc Vol mm³ | Vol mm³ | Flow Time sec |
|---|---|---|---|---|---|
| 5 | 0.090 | 0.206 | 0.13 | 0.127 | 0.62 |
| 10 | 0.090 | 0.103 | 0.13 | 0.254 | 1.85 |
| 15 | 0.090 | 0.069 | 0.13 | 0.382 | 3.70 |
| 20 | 0.092 | 0.056 | 0.13 | 0.515 | 6.11 |
| 25 | 0.099 | 0.056 | 0.16 | 0.671 | 8.91 |
| 30 | 0.106 | 0.056 | 0.18 | 0.846 | 12.06 |
| 35 | 0.111 | 0.056 | 0.19 | 1.040 | 15.56 |
| 40 | 0.116 | 0.056 | 0.21 | 1.253 | 19.38 |
| 45 | 0.121 | 0.056 | 0.23 | 1.482 | 23.51 |
| 50 | 0.125 | 0.056 | 0.25 | 1.729 | 27.95 |
| 55 | 0.129 | 0.056 | 0.26 | 1.992 | 32.68 |
| 60 | 0.133 | 0.056 | 0.28 | 2.270 | 37.68 |
| 65 | 0.137 | 0.056 | 0.29 | 2.563 | 42.97 |
| 70 | 0.140 | 0.056 | 0.31 | 2.872 | 48.52 |
| 75 | 0.143 | 0.056 | 0.32 | 3.195 | 54.33 |
| 80 | 0.147 | 0.056 | 0.34 | 3.532 | 60.40 |
| 85 | 0.149 | 0.056 | 0.35 | 3.883 | 66.72 |
| 90 | 0.152 | 0.056 | 0.36 | 4.248 | 73.28 |
| 95 | 0.155 | 0.056 | 0.38 | 4.626 | 80.08 |
| 100 | 0.158 | 0.056 | 0.39 | 5.017 | 87.12 |
| 105 | 0.160 | 0.056 | 0.40 | 5.421 | 94.40 |
| 110 | 0.163 | 0.056 | 0.42 | 6.838 | 101.90 |
| 115 | 0.165 | 0.056 | 0.43 | 6.267 | 109.63 |
| 120 | 0.168 | 0.056 | 0.44 | 6.709 | 117.58 |
| 125 | 0.170 | 0.056 | 0.45 | 7.163 | 125.75 |
| 130 | 0.172 | 0.056 | 0.47 | 7.629 | 134.13 |
| 135 | 0.174 | 0.056 | 0.48 | 8.107 | 142.73 |
| 140 | 0.177 | 0.056 | 0.49 | 8.596 | 151.55 |
| 145 | 0.179 | 0.056 | 0.50 | 9.098 | 160.56 |
| 150 | 0.181 | 0.056 | 0.51 | 9.610 | 169.79 |
| 155 | 0.183 | 0.056 | 0.52 | 10.134 | 179.22 |
| 160 | 0.185 | 0.056 | 0.54 | 10.669 | 188.85 |

It is evident from the above table that the path may change from a capillary of constant radius, to one in which the radius increases (e.g., a funnel) or decreases with distance. This formula can be used to vary velocity as desired as the liquid moves down the capillary track or through a region of reagent. One could even envision a pulsating flow.

In accordance with the subject invention, novel devices and methods are provided for measuring a wide variety of sample characteristics including analytes of interest. The devices provide for simple measurement or volumes, mixing of reagents, incubations, and visual or instrumental determination of the result. The detection system may involve the absorption or emission of light, or modulation of flow, including slowing, stoppage, or their reversal. Of particular interest is the use of blood where clotting can be determined or reagents affecting clotting. Also of interest are a wide variety of analytes, which include naturally-occurring compounds or synthetic drugs. The devices allow for the simultaneous performance of controls and comparison of signals from the two media. In addition, various combinations of channels and chambers may be employed, so that the pathways can diverge and converge, be broken up into a plurality of different pathways or a sample may be divided into a plurality of paths and treated in a variety of ways. The devices can be simple to fabricate and the serpentine paths readily devised by employing known fabrication techniques, with particularly advantageous devices being available through use of the preferred fabrication techniques described herein.

The following examples are offered by way of illustration and not by way of limitation.

EXPERIMENTAL

EXAMPLE 1: Detection of Prothrombin Time

A device or cartridge analogous to the device of FIG. 5 is employed. Two pieces of cellulose acetate 40 mil thick are separated by scored Fason TM fast tape B to provide the proper design of channels and chambers. The reaction chamber contains a thromboplastin reagent where an aqueous solution of the thromboplastin is introduced into the chamber, the water evaporated, leaving the chamber coated with thromboplastin. The thromboplastin reagent composition is: 15 mg/ml rabbit brain thromboplastin extract; 1% glycine; 0.01% thimerosol; 0.01% streptomycin-sulfate; 0.01% triton X100; 0.08% phenol; 1% polyethylene glycol 3500; 4% sucrose; 0.001% Polybrene TM (1,5-dimethyl-1,5-diazaundecamethylene polymethobromide). The mixture is lyophilized and reconstituted to 0.25 original volume with deionized water. Three µl of the reconstituted liquid is then placed on the reagent area of the device and then allowed to air dry before attaching the other sheet or cover of the device. A cover is then placed over the chambers and channels, and a 15 µl blood sample is introduced into the receiving chamber. The device is then inserted into a monitor which may be thermostatted at 25° C. or 37° C., where a gallium arsenide semiconductor laser of wavelength 0.78 µ directs a beam at a site between the ends of the channel joining the receiving chamber and the reaction chamber. On the opposite side from the laser is a silicon photodetector of a small area sufficient to detect the oscillating speckled pattern resulting from the red blood cells flowing through the channel. A DC signal is observed with large fluctuations. The DC signal is inversely proportional to the red cell density, and fluctuation continues until clotting occurs. The time is then related to known standards to determine the clotting characteristic of the blood. Where warfarin is being administered to the blood source, the time for clotting can be related to the effect of warfarin on the blood clotting time. In addition, the light absorbance in the channel can be determined to provide for a hematocrit, as a further characteristic of the blood sample. Because of the short path length of the light, undiluted blood can be used which provides a further convenience.

EXAMPLE 2: Detection of Cross-linked Fibrin Dimer by Latex Agglutination

Materials: "Dimertest latex" reagents and control serum (MABCO Ltd). A cartridge analogous to that of FIG. 5 is used. Two flat pieces of polystyrene formed by injection moulding are welded together to form the capillary channel and reagent chamber. The receiving chamber (166) is 0.467 cm wide by 0.09 cm deep. The first capillary channel (168) is 1.3 mm wide by 0.09 mm deep. The reagent chamber (176) is a elipse of major axis 12 mm and minor axis 6 mm and is 0.09 mm deep. The serpentine capillary path (172) is 160 mm long tapering from a radius of 0.09 mm at the outlet of the reagent chamber to 0.185 mm at the outlet port (180).

Experimental: Sample (10 µl of either buffer or positive control) was mixed with antibody coated latex (40 µl); after 3' gentle shaking 40 µl of the mixture was injected into the cartridge containing no reagent and inserted into a monitor as described in Example 1. The signal from the laser detector was recorded on an Omega chart recorder (model 1202) using 5 V full scale sensitivity and a chart speed of 6 cm/min. The movement of latex particles through the light beam produced a slightly noisy trace (~1 chart division {0.01 full scale} peak-peak). Agglutination of the latex caused by the presence of the analyte (cross-linked fibrin degradation products) resulted in a significant increase in noise (~3 chart divisions peak-peak).

EXAMPLE 3: Direct Blood Grouping by Red Blood Cell Agglutination

Materials: Human blood samples of known groups anticoagulated with sodium citrate. Blood grouping antisera (American Dade).

Experimental: Resuspended blood (40 µl) was mixed with antiserum (40 µl) and 40 µl of the mixture injected into empty cartridges (as in example 2) and results analyzed as in Example 2. Positive agglutination was observed as a rapidly increasing noise level, negative reactions gave a steady, low, noise level.

EXAMPLE 4: Direct blood grouping by flow stop

Materials: Blood samples as in Example 3. Cartridges as described in Example 2 were employed. Before welding the two parts of the cartridge, the serpentine track of the lower part was evenly coated with 5µl blood typing anti-serum (American Dade) which had been dialysed against 1% glycine (Na−) pH 7.5 containing 0.01% Triton X-100, 2% sucrose and 0.5% polyethylene glycol −3500. Solvent (water) was then removed by evaporation and the two parts of the cartridge welded together.

Experimental: Blood (40 µl) was injected into the cartridges after insertion in a monitor (described in example 1). The time for flow of red blood cells past the laser beam to stop was recorded.

| Blood # | Group | Reagent | Time (s) | Positive or Negative* |
|---------|-------|---------|----------|------------------------|
| 1 | A | A | 43 | + |

| Blood # | Group | Reagent | Time (s) | Positive or Negative* |
|---|---|---|---|---|
| | | B | 175 | − |
| 3 | A | A | 69 | + |
| | | B | 190 | − |
| 4 | B | A | >270 | − |
| | | B | 58 | + |
| 8 | O | A | >200 | − |
| | | B | >187 | − |

*A positive reaction was defined as Time < 120 s.

Agglutination of red blood cells at the leading edge of the blood caused clogging of the track and flow stop. All the blood samples gave the appropriate reaction.

EXAMPLE 5: Blood grouping by flow rate measurements

Materials: Blood samples as in Example 3; Cartridges (as described in example 2) with 3 μl American Dade blood typing antisera applied (as described in example 4) to the reagent chamber and dried.

Experimental: Blood (50 μl) was injected into the cartridges at room temperature. The time taken for the blood to reach known distances along the narrow track was recorded. Flow rates were then calculated from a knowledge of the cross section of the track as a function of distance.

| Blood Sample # | Group | Reagent | Flow Rate at 150 s (mm³/s) | Positive or Negative |
|---|---|---|---|---|
| 6 | B | A | 0.045 | − |
| | | B | 0.025 | + |
| 1 | A | A | 0.018 | + |
| | | B | 0.045 | − |
| 8 | O | A | 0.047 | − |
| | | B | 0.047 | − |

*A positive reaction was taken as flow rate < 0.030 mm³/s.

Agglutination of red blood cells caused a significant reduction in flow rates.

EXAMPLE 6: Use of filters to modify sample composition a. Red cells were quantitatively removed from whole blood by filtration through a dry filter paper disc impregnated with anti human red cells. Discs were cut to fit the sample application site of cartridges from Beckman Paragon ® electrophoresis blotter paper (about 0.57 mm thick). A metal punch of diameter 0.467 cm was used. After the discs were snugly inserted in the sample cite of the track, 10 μl rabbit anti-human red cells (Cappel) was added. This is enough liquid to saturate the paper. The liquid was then evaporated under vacuum.

When blood (40 μl) was applied to the disc about 7 μl clear plasma emerged into the track before flow stopped.

b. Filter paper disc (as above) impregnated with sodium deoxycholate (10 μl×10%) were dried under vacuum and placed in the sample application site. Blood (40 μl) was applied at 37° C. A clear uniform red solution free of all red cells filtered into and filled the track. The absorbance of the remaining hemolysate can give an accurate hemoglobin concentration.

EXAMPLE 7: Electronic Cartridge

An electronic cartridge capable of simulating the flow of whole blood through a capillary was prepared using a 32768 Hz crystal-controlled oscillator to drive two 1–16th frequency dividers that generated the input signals for a driver of a liquid crystal display cell prepared in accordance with the electronic diagram set forth in FIG. 7. This cell was biased by a 2048 Hz signal modulated at 128 Hz intervals. The cell therefore rotated its polarization at the rate of 128 Hz.

Two more dividers drove a logical AND gate whose output was to a logic low every 20 seconds. At this point, the output of a logical OR gate reset the dividers, stopping the process. Accordingly, the LCD was powered and modulating for a 20-second interval.

A start switch was provided to clear the reset signal and restart the process. The oscillators, dividers, logic gates, and LCD driver were implemented in CMOS technology and powered by a coin-type lithium battery. The electronic cartidge has a life of more than 10,000 cycles.

EXAMPLE 8: Out-of-Blood Detector

The following sample depletion device was prepared in the manner shown in FIG. 8. An infrared LED was embedded into the surface of the analytical device into which a capillary flow cartridge was to be inserted so that the output of its light would impinge upon the blood reservoir 1 mm from the capillary entrance. The LED is powered by an operational amplifier configured as a square wave generator of about 8 KHz. An infrared-sensitive photodetector was located 2 mm from the junction of the sample reservoir and the capillary channel. The signal output of the detector was passed to a band-pass filter having a center at 8 KHz and a bandwidth of 500 Hz and was further amplified by an amplifier. The amplified signal was rectified and integrated, thereby generating a direct current voltage proportional to the scattered light.

When a blood sample is added to the reservoir and flows by capillary action through the capillary into other portions of the test cartridge, the light path between the LED and the photodetector is interrupted when the reservoir empties. When the voltage output of the integrator falls below 50–30 millivolt, the input of this voltage into a comparator will indicate the absence of blood in the blood reservoir.

EXAMPLE 9: Fabrication

Plastic cartridges were injection molded out of Cycolac ® CTB Resin (acrylanitrile-butadiene-styrene copolymer) obtained from Borg-Warner Chemicals, Inc. The design of the cartridge capillary channel and overall structure is similar to that shown in FIG. 5 in that it contains a sample reservoir, an initial short capillary, a reagent chamber and a second long capillary. However, the configuration of the actual chambers and capillaries differ from those shown. The cartridge consisted of a 30-mil base and a 30-mil cover. Both the cover and base were plasma etched in an LFE Model 1002 Plasma system with the following settings: argon pressure, 2 torr; argon flow, 1–3; forward RF powere, 100; etch time, 20 minutes. Three microliters of Biotrack thromboplastin reagent were then applied to the base of the oval area at the base of the cartridge and allowed to dry for 10 minutes in an environment kept at 25° C. and 10% relative humidity. The etched cover was then placed on the base and welded thereto using a Branson 8400Z ultrasonic welder with the following settings: down speed, 3 seconds; hold time, 0.5 seconds; weld energy, 0.5 Kjoule; and weld time, 0.26–0.30 second.

Following fabrication, the cartridges were tested with whole blood controls (both abnormal and normal clotting times), which are described in a copending application filed on even date with this application entitled "Whole Blood Control Sample" using the Biotrack Model Monitor 1000. The prothrombin times were recorded. In addition, the flow rate of blood in a cartridge without reagent was measured.

The results of the test were subjected to statistical analysis. When replicates were run, the mean and coefficient of variation were 12.3 seconds and 4.9% for the normal control and 20.0 seconds and 2.9% for the abnormal control. The flow rate of blood in the capillary channel four days later was constant at 0.06 mm$^3$/sec. These results are quite superior to other fabrication techniques described in this specification, including the example using tape set forth in Example 1, which gave C.V.s in the 10–20% range.

All publications and patent applications mentioned in this specification are indicative of level of skill of those skilled in the art to which this invention pertains and are herein incorporated by reference to the same extent as if each individual patent application and publication had been individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An analytical device for detecting the presence of an analyte in a physiological fluid sample, comprising:
   a housing containing an inlet port, a chamber unit, an exit port, a first capillary unit for independently pumping a liquid from said inlet port to said chamber unit, and a second capillary unit positioned between and operatively connected to said chamber unit and said exit port for independently pumping a liquid from said chamber unit to said exit port; wherein said inlet port, first capillary unit, chamber unit, second capillary unit, and exit port are present in a continuous capillary pathway; said housing further containing a reagent in said capillary pathway comprising a member selected from the group consisting of compounds affecting blood clotting and antibodies capable of causing a change in flow rate of said fluid sample in said pathway.

2. The device of claim 1, wherein said reagent comprises an antibody.

3. The device of claim 1, wherein said device comprises at least two chamber units in said pathway.

4. The device of claim 1, further comprising a sealable vent in said capillary pathway proximal to a juncture between a chamber unit and a capillary unit.

5. The device of claim 1, further comprising a third capillary unit substantially in parallel with said first capillary unit and directing fluid into said chamber unit.

6. The device of claim 1, wherein said reagent comprises a member selected from the group consisting of components of natural blood clotting cascades and reagents which activate a components of a natural clotting cascade.

7. The device of claim 6, wherein said reagent is thromboplastin.

8. The device of claim 1, wherein said housing comprises a substantially hydrophobic material having at least a portion of the walls of said capillary pathway treated to provide hydrophilicity.

9. The device of claim 8, wherein said material is a plastic.

10. The device of claim 1, said device being fabricated from at least two sheets of a substantially hydrophobic plastic, at least one of which is molded to provide depressions for production of said capillary and chamber units, said depressions being treated to provide hydrophilicity, wherein at least one sheet has means defining an orifice forming said inlet port or exit port, said capillary and chamber units being formed by the joining of said sheets to form said housing.

11. The device of claim 10, wherein said chamber unit contains said reagent and said reagent comprises a member selected from the group consisting of components of natural clotting cascades and reagents which activate a component of a natural clotting cascade.

12. The device of claim 10, wherein said reagent comprises thromboplastin in said chamber unit.

* * * * *